(12) United States Patent
Li et al.

(10) Patent No.: US 12,011,426 B2
(45) Date of Patent: Jun. 18, 2024

(54) METHODS OF METABOLIC REGULATION OF MITOCHONDRIA FOR TREATING NEURAL INJURY AND NEUROLOGICAL DISORDERS

(71) Applicant: The USA, as represented by the Secretary, Dept. of Health and Human Services, Bethesda, MD (US)

(72) Inventors: Wei Li, Bethesda, MD (US); Tantai Zhao, Hunan (CN); Jingxing Ou, Guangdong (CN)

(73) Assignee: THE USA, AS REPRESENTED BY THE SECRETARY, DEPT. OF HEALTH AND HUMAN SERVICES, Bethesda, MD (US)

( * ) Notice: Subject to any disclaimer, the term of this patent is extended or adjusted under 35 U.S.C. 154(b) by 647 days.

(21) Appl. No.: 17/268,203

(22) PCT Filed: Aug. 21, 2019

(86) PCT No.: PCT/US2019/047504
§ 371 (c)(1),
(2) Date: Feb. 12, 2021

(87) PCT Pub. No.: WO2020/041470
PCT Pub. Date: Feb. 27, 2020

(65) Prior Publication Data
US 2021/0161845 A1 Jun. 3, 2021

Related U.S. Application Data

(60) Provisional application No. 62/720,612, filed on Aug. 21, 2018.

(51) Int. Cl.
*A61K 31/194* (2006.01)
*A61K 31/23* (2006.01)

(52) U.S. Cl.
CPC ............ *A61K 31/194* (2013.01); *A61K 31/23* (2013.01); *C12Y 103/05001* (2013.01)

(58) Field of Classification Search
CPC .................. A61K 31/194; A61K 31/23; C12Y 130/05001
See application file for complete search history.

(56) References Cited

U.S. PATENT DOCUMENTS

2005/0197397 A1* 9/2005 Martin .................... A61P 17/18
514/557
2012/0258989 A1 10/2012 Rieck et al.
(Continued)

FOREIGN PATENT DOCUMENTS

CN 108295068 7/2018
EP 1006112 6/2000
(Continued)

OTHER PUBLICATIONS

Mills et al: "Succinate Dehydrogenase Supports Metabolic Repurposing of Mitochondria to Drive Inflammatory Macrophages", Cell, Elsevier, vol. 167, No. 2, 2016, p. 457.*
(Continued)

*Primary Examiner* — Deborah D Carr
(74) *Attorney, Agent, or Firm* — McDonnell Boehnen Hulbert & Berghoff LLP

(57) ABSTRACT

Methods are disclosed for treating and/or preventing a neurological condition, such as neural injury or neurological disorder, in a subject through metabolic regulation of mitochondria using compounds that are natural metabolites, metabolite analogs, or derivatives of natural metabolites to modulate biochemical pathways comprising succinate and/or succinate dehydrogenase, thereby reducing microglial cell and/or astrocyte activation. Compounds and related formulations are also provided to modulate the biochemical pathways comprising succinate and/or succinate dehydro-
(Continued)

isocitrate ⟶ α-ketoglutarate ⟶ Succinyl-CoA ⟶ succinate ⟷ fumarate ⟷ malate
                                                                    SD γ-aminobutyric acid ⟶ Succinic semialdehyde (SSA) ⟶ succinate ⟷ fumarate
                                                             SD propionyl-CoA ⟶ D-methylmalonyl-CoA ⟷ L-methylmalonyl-CoA ⟷ Succinyl-CoA succinate ⟷ fumarate
         SD genase for reducing or inhibiting microglial cell and/or astrocyte activation.

12 Claims, 9 Drawing Sheets

(56) References Cited

U.S. PATENT DOCUMENTS

| | | |
|---|---|---|
| 2017/0107380 A1 | 4/2017 | Polson et al. |
| 2017/0135977 A1 | 5/2017 | Chouchani et al. |

FOREIGN PATENT DOCUMENTS

| | | | |
|---|---|---|---|
| WO | WO 2006/066244 | 6/2006 | |
| WO | WO-2006066244 A2 * | 6/2006 | ............. A23L 33/10 |
| WO | 2006086643 A1 | 8/2006 | |
| WO | WO 2016/001686 | 1/2016 | |
| WO | WO-2016001686 A1 * | 1/2016 | ........... A61K 31/225 |
| WO | 2017142855 A1 | 8/2017 | |
| WO | WO 2017/142855 | 8/2017 | |
| WO | WO-2017142855 A1 * | 8/2017 | ............. A61K 31/19 |
| WO | WO 2019/036509 | 2/2019 | |

OTHER PUBLICATIONS

Ruban et al: "Combined Treatment of an Amyotrophic Lateral Sclerosis Rat Model with Recombinant GOT1 and Oxaloacetic Acid: A Novel Neuroprotective Treatment", Neurodegenerative Diseases, vol. 15, No. 4, 2015, pp. 233-242.*
Mirandola et al: "Methylmalonate inhibits succinate-supported oxygen consumption by interfering with mitochondrial succinate uptake", Journal of Inherited Metabolic Disease, vol. 31, No. 1, 2008, pp. 44-54.*
Brown et al. "Regulation of succinate-fuelled mitochondrial respiration in liver and skeletal muscle of hibernating thirteen-lined ground squirrels," The Journal of Experimental Biology, 2013, vol. 216, pp. 1736-1743.
Kohlhauer et al. "Protection against cardiac ischemia-reperfusion injury by hypothermia and by inhibition of succinate accumulation and oxidation is additive," Basic Research in Cardiology, May 2019, vol. 114, No. 3, Article 18, 9 pages.
Liddelow et al. "Neurotoxic reactive astrocytes are induced by activated microglia," Nature, Jan. 2017, vol. 541, No. 7638, pp. 481-487.
Mills et al. "Succinate Dehydrogenase Supports Metabolic Repurposing of Mitochondria to Drive Inflammatory Macrophages," Cell, Oct. 2016, vol. 167, No. 2, pp. 457-470.
Mirandola et al. "Methylmalonate inhibits succinate-supported oxygen consumption by interfering with mitochondrial succinate uptake," Journal of Inherited Metabolic Disease, Jan. 2008, vol. 31, No. 1, pp. 44-54.
Orihuela et al. "Microglial M1/M2 polarization and metabolic states," British Journal of Pharmacology, 2016, vol. 173, pp. 649-665.
Peruzzotti-Jametti et al. "Macrophage-Derived Extracellular Succinate Licenses Neural Stem Cells to Suppress Chronic Neuroinflammation," Cell Stem Cell, Mar. 2018, vol. 22, pp. 355-368.
Ruban et al. "Combined Treatment of an Amyotrophic Lateral Sclerosis Rat Model with Recombinant GOT1 and Oxaloacetic Acid: A Novel Neuroprotective Treatment," Neuro-degenerative Diseases, Jun. 2015, vol. 15, No. 4, pp. 233-242.
Rustin et al. "Succinate dehydrogenase and human diseases: new insights into a well-known enzyme," European Journal of Human Genetics, 2002, vol. 10, pp. 289-291.
Shchepinova et al. "MitoNeoD: A Mitochondria-Targeted Superoxide Probe," Cell Chemical Biology, Oct. 2017, vol. 24, No. 10, pp. 1285-1298.
Xu et al. "Inhibiting Succinate Dehydrogenase by Dimethyl Malonate Alleviates Brain Damage in a Rat Model of Cardiac Arrest," Neuroscience, Oct. 2018, vol. 393, pp. 24-32.
International Search Report and Written Opinion for International (PCT) Patent Application No. PCT/US2019/047504, dated Dec. 3, 2019 16 pages.
Office Action issued in corresponding Chinese Patent Application No. 201980061762.3, dated Jul. 28, 2023, 8 pages (English language translation included).

* cited by examiner

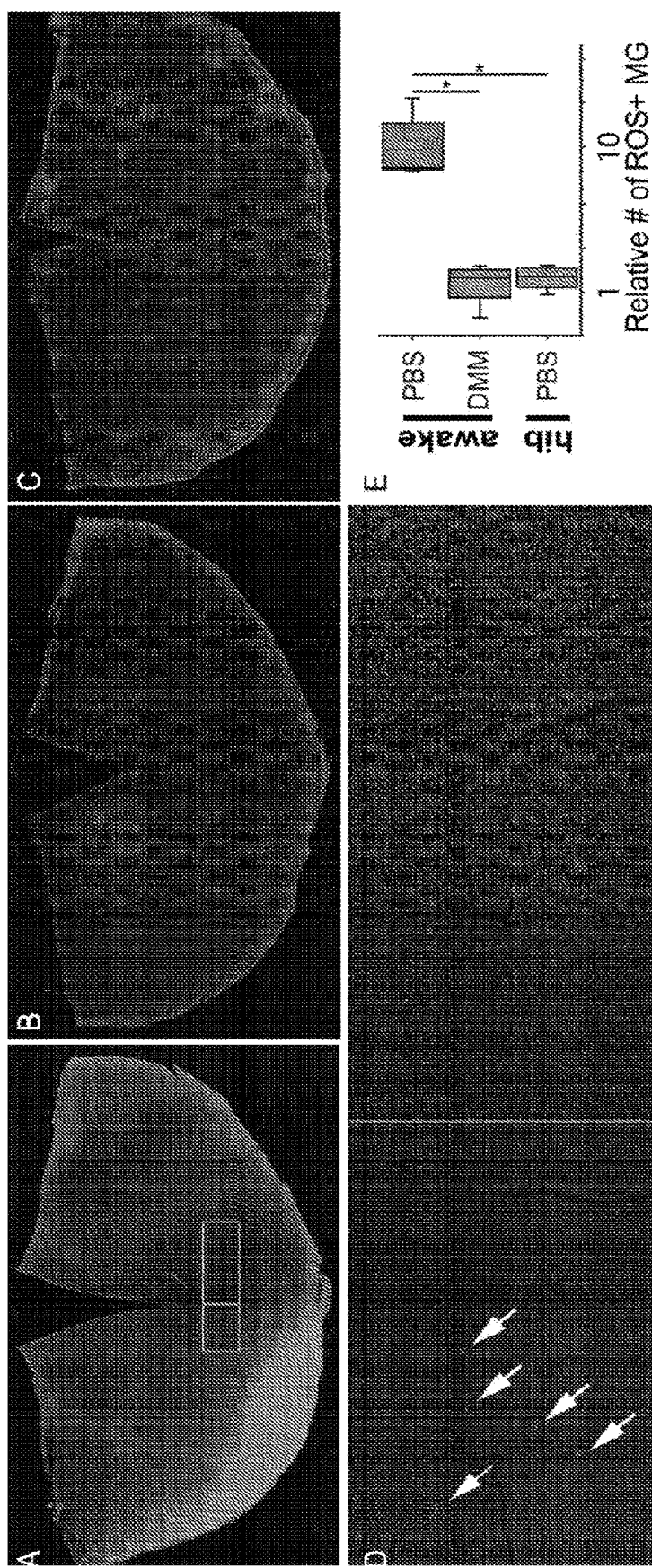
FIG. 6A-E

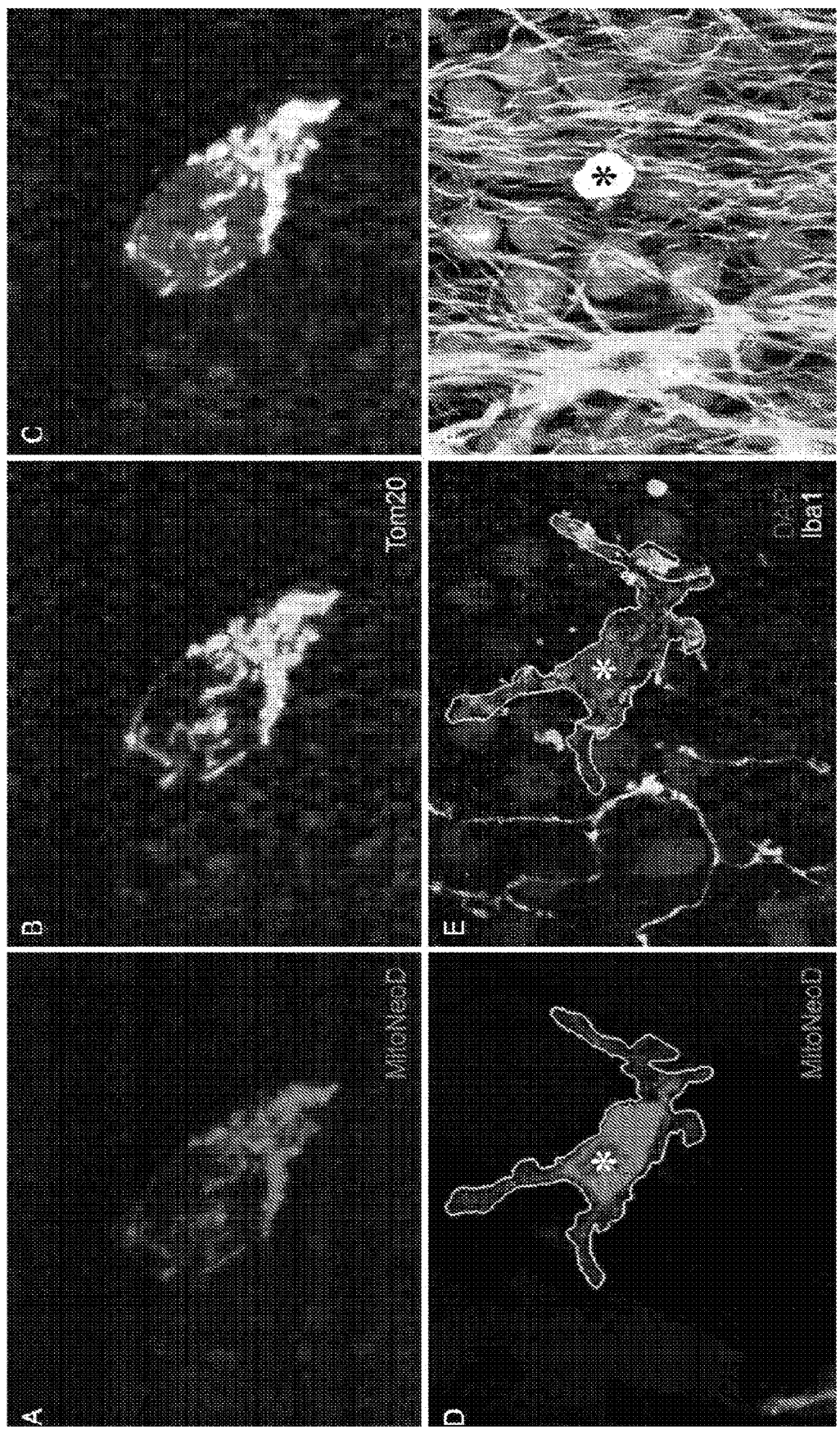
FIG. 7A-F

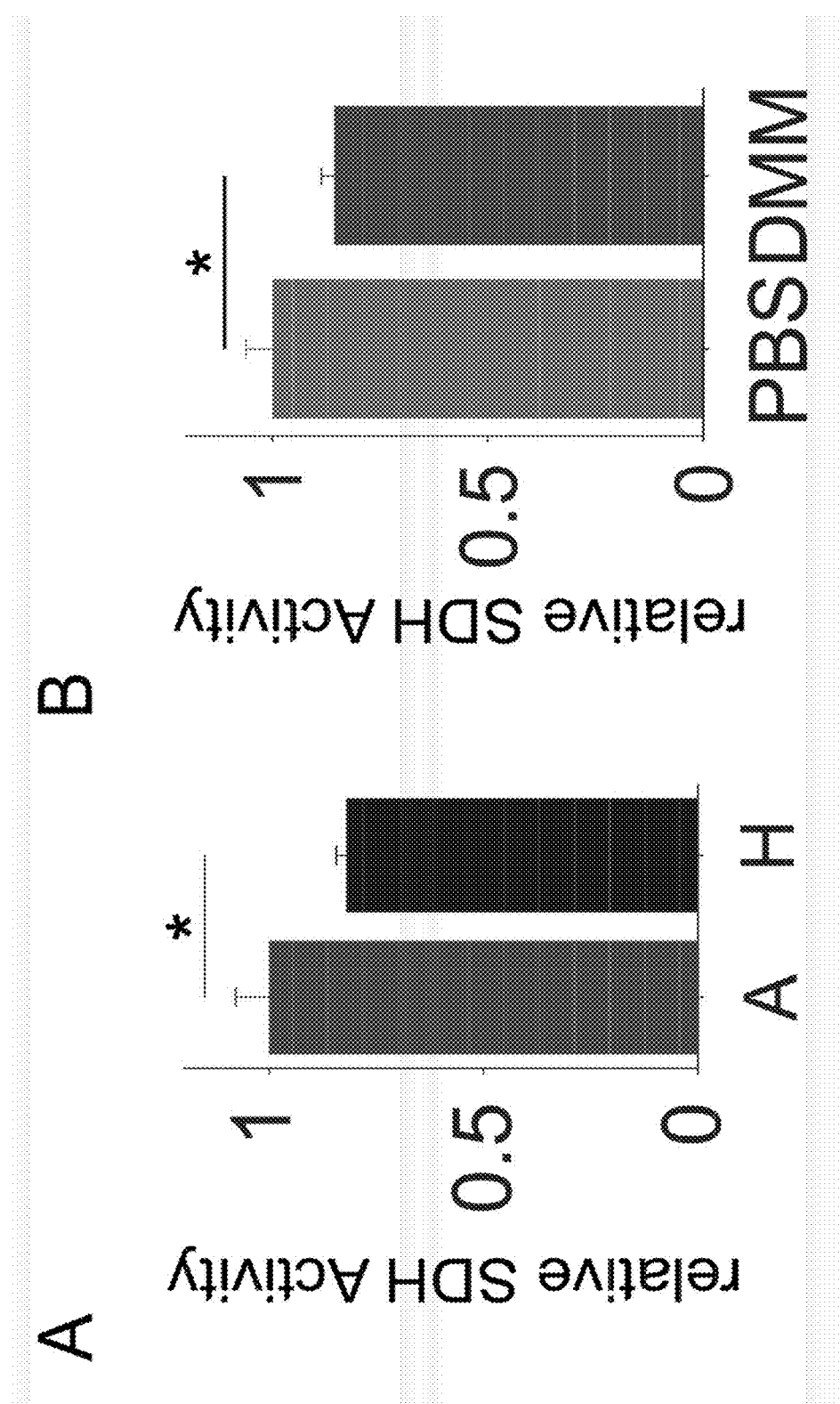
FIG. 8A-B

METHODS OF METABOLIC REGULATION OF MITOCHONDRIA FOR TREATING NEURAL INJURY AND NEUROLOGICAL DISORDERS

CROSS REFERENCE TO RELATED APPLICATIONS

This application is a national stage application under 35 U.S.C. 371 and claims the benefit of PCT Application No. PCT/US2019/047504 having an international filing date of 21 Aug. 2019, which designated the United States, which PCT application claimed the benefit of U.S. Provisional Patent Applications Ser. No. 62/720,612, filed 21 Aug. 2018, the contents of each of which are incorporated herein by reference in their entirety.

FIELD OF THE INVENTION

The invention relates to the field of treatment and/or prevention of a neurological condition, such as neural injury or neurological disorder, through metabolic regulation of mitochondria using compounds that are natural metabolites, metabolite analogs, or derivatives of natural metabolites to modulate biochemical pathways comprising succinate and/or succinate dehydrogenase, thereby reducing microglial cell and/or astrocyte activation.

BACKGROUND

Each year, hundreds of millions of people worldwide are affected by neurological disorders or neural injuries. Such neurological conditions can cause devastating functional loss, with concomitant financial loss and a severe reduction in quality of life. It is estimated that, globally, there are 47.5 million people with dementia, with 7.7 million new cases being diagnosed every year. Alzheimer's disease is the most common cause of dementia and may contribute to 60-70% of such cases. Parkinson's is the second most common age-related neurodegenerative disorder after Alzheimer's disease. An estimated seven to ten million people worldwide suffer from Parkinson's disease. Additionally, more than 50 million people worldwide have epilepsy and the prevalence of migraine headaches is more than 10%.

It is believed that microglia and/or astrocyte-initiated inflammation plays a critical role in the process of developing or worsening at least some neurological disorders. More specifically, it has been proposed that neural injury, or degeneration, triggers the activation of microglial cells, which in turn release cytokines that activate astrocytes, which then kill injured neurons. Thus, targeting microglial cells, or cytokines released therefrom, appears to be a promising strategy for treating neural injury and/or neural degeneration. However, currently available interventions for microglial inhibition have limited beneficial effects. Thus, there is a need for improved methods for treating and/or preventing neurological disease.

Recently, the inventors discovered that succinate dehydrogenase (SDH), a key mitochondria enzyme, is regulated in the ground squirrel retina during hibernation, and that this regulation contributes to microglia inactivation during hibernation. The present disclosure therefore provides a method of regulating the immune system by modulation of pathways comprising succinate and/or succinate dehydrogenase. Such methods are useful for treating or preventing neurological damage.

SUMMARY

The inventors have discovered that metabolic adaptation during hibernation (including lower succinate levels) leads to local immune suppression (including lower microglial and astrocyte activity), which in turn protects neurons from death after axonal injury. The results further suggest that mimicking hibernation through pharmacological means is a useful method of neural protection.

This disclosure therefore provides methods of treating or slowing the progression of a neurological condition, such as neural injury or neurological disorder, by reducing or inhibiting the neuroimmune response. More specifically, the disclosure provides methods for reducing the neuroimmune response by reducing the levels of succinate, and/or reducing the level or activity of succinate dehydrogenase, in an individual. Accordingly, compounds and related formulations are provided to modulate biochemical pathways comprising succinate and/or succinate dehydrogenase, thereby reducing microglial cell and/or astrocyte activation, and treating neurological injuries and neurological disorders.

The methods include administering to a subject in need of such treatment an effective amount of at least one compound that reduces the level of succinate, or reduces the level or activity of succinate dehydrogenase, in the subject. The compound may modulate a biochemical pathway comprising succinate, and/or succinate dehydrogenase, which may reduce or prevent the activation of microglial cells, including for example reducing or preventing the release of cytokines from microglial cells. This may also reduce or prevent activation of astrocytes.

Modulation of the biochemical pathway may include modulation of any enzyme in the biochemical pathway that is necessary for the production of succinate. Alternatively, modulation of the biochemical pathway may include modulation of any enzyme in the biochemical pathway that is necessary for the catabolism of succinate. Methods may also include inhibition of any enzyme necessary for the synthesis or catabolism of succinate.

Modulation of the biochemical pathway may also include modulation of an enzyme upstream of succinate dehydrogenase in the biochemical pathway and/or modulation of the activity of an enzyme downstream of succinate dehydrogenase in the biochemical pathway. Modulation may also include reducing or inhibiting the activity of succinate dehydrogenase. The biochemical pathway may comprise any one or more of succinate, fumarate, succinic semialdehyde (SSA), γ-aminobutyric acid, succinyl-CoA, methylmalonyl CoA, or α-ketoglutarate (α-KG).

The administered compound may act directly on succinate dehydrogenase, and may be a molecule from the biochemical pathway comprising succinate dehydrogenase, or a prodrug, or active metabolite, analog or derivative thereof. Exemplary compounds with these activities include dimethyl malonate (DMM), oxaloacetic acid, octyl itaconate, or an active metabolite, analog, and derivatives thereof.

In these treatment methods, the neurological condition, such as a neural injury or neurological disorder, may be the result of or encompass an immune response as part of the etiology of the neurological disease or disorder or response to neurological trauma. Such immune response may comprise microglial cells and/or astrocytes.

The neurological condition may be a congenital neurological disorder, or may be due to a toxin, a nutritional deficiency, an infection, or traumatic brain injury, a spinal cord injury, or a neoplasm, but these neurological disorders do not include hypoxia or stroke. The neurological disorder may be a neurodegenerative disease such as Alzheimer's disease, Parkinson's disease, amyotrophic lateral sclerosis, or multiple sclerosis.

In these methods, the administration of the compound may result in the reduction or prevention of neuronal damage.

The methods also include reducing or preventing neuronal damage in a subject by administering to the subject a compound that reduces the level of succinate, or reduces the activity of succinate dehydrogenase, in the subject. The compound may inhibit the production of succinate, or may increase the catabolism of succinate. The compound may inhibit succinate dehydrogenase.

The methods also include inhibiting the activation of a microglial cell by contacting the cell with a compound that reduces the level of succinate in the cell, or that reduces the activity of succinate dehydrogenase in the cell. The compound may inhibit the production of succinate, or may increase the catabolism of succinate. The compound may inhibit succinate dehydrogenase. The cell may be in an organism (e.g., a mammal), or it may be a cell in culture (i.e., in vitro).

The disclosure also includes methods of reducing or preventing the release of cytokines from a microglial cell by contacting a microglial cell with a compound that reduces the level of succinate in the cell, or that reduces the activity of succinate dehydrogenase in the cell. The compound may inhibit the production of succinate, or may increase the catabolism of succinate. The compound may inhibit succinate dehydrogenase. The cell may be in an organism, or it may be a cell in culture.

The disclosure also includes methods of reducing or preventing the activation of an astrocyte in a system comprising a microglial cell and an astrocyte, such methods comprising introducing into the system a compound that reduces the level of succinate in the cell, or that reduces the activity of succinate dehydrogenase in the cell. The compound may inhibit the production of succinate, or may increase the catabolism of succinate. The compound may inhibit succinate dehydrogenase. The microglial cell and the astrocyte may be in an organism, or they may be in a culture (i.e., in vitro).

This Summary of methods of treatment and prevention of neurological condition is neither intended nor should it be construed as being representative of the full extent and scope of the present invention. Moreover, references made herein to "the present invention," or aspects thereof, should be understood to mean certain embodiments of the present invention and should not necessarily be construed as limiting all embodiments to a particular description. The present invention is set forth in various levels of detail in this Summary as well as in the attached drawings and the Description and no limitation as to the scope of the present invention is intended by either the inclusion or non-inclusion of elements, components, etc. in this Summary. Additional aspects of the present invention will become more readily apparent from the Description, particularly when taken together with the figures.

BRIEF DESCRIPTION OF THE FIGURES

FIG. 2A shows significantly decreased levels of succinate in the retinal tissues during deep hibernation. FIG. 2B shows increased levels of succinylcarnitine in these retinal tissues.

FIG. 5A shows the results of RGC survival after optic nerve crush (ONC) in active animals, hibernating animals, active animals pretreated with PLX5622 to eliminate microglial cells (and hence acute inflammatory responses), and in active animals with repeating pretreatments and treatments of DMM to inhibit succinate hydrogenase prior to and after the ONC injury. FIG. 5B shows the results that with the addition of DMM to 1 (LD1=100 ng/ml LPS+1 mM DMM) mM or 10 (LD10=100 ng/ml LPS+10 mM DMM) mM, production of pro-inflammatory cytokines such as MCP-1 and IL1A was significantly reduced in cultured microglial cells after exposing to LPS (a bacterial toxin that can induce inflammatory activation of microglial cells).

FIGS. 6A-6E show levels of reactive oxygen species (ROS) in the injured side of the retina following partial optic nerve crush (ONC) in thirteen lined ground squirrels (TLGS). ROS is visualized using the mitochondrial dye MitoNeoD (Schepinova et al. 2017). FIGS. 6A and 6B show the level of ROS on the injured side of the retina in active (FIG. 6A) and torpid (FIG. 6B) TLGS, respectively. FIG. 6C shows the level of ROS in active TLGS treated with dimethyl malonate (DMM). FIG. D is a magnified section of the retina shown in FIG. C. Arrows point to MitoNeoD+ cells, indicating microglial cells. The gray line marks the boundary of crushed and uncrushed area. FIG. 6E shows the relative number of ROS+ cells by the ratio of MitoNeoD+ cells in the crush side over those in the uncrushed side for awake, awake with DMM injection, and hibernating (hib) samples.

FIGS. 7A-F. FIGS. 7A-7C show MitoNeoD signals (FIG. 7A; red) colocalizing with Tom20 (green), a mitochondrial marker, and Dap-1. FIGS. 7D-7E show MitoNeoD signals (red; 7D) are high in microglial cells labeled with Iba1 antibody (green; 7E). Panel F is a 3D rendering illustrating that this microglial cell locates above the astrocytic processes (cyan, GFAP antibody), where optic nerve fibers are found.

FIGS. 8A & 8B show biochemical measurements of SDH activity TLGS. FIG. shows SDH activity in awake (A), and hibernating (H) LTGS. FIG. B shows SDH activity in awake animals treated with phosphate buffered saline (PBS)(left) or DMM (right).

DETAILED DESCRIPTION

Figure 1:
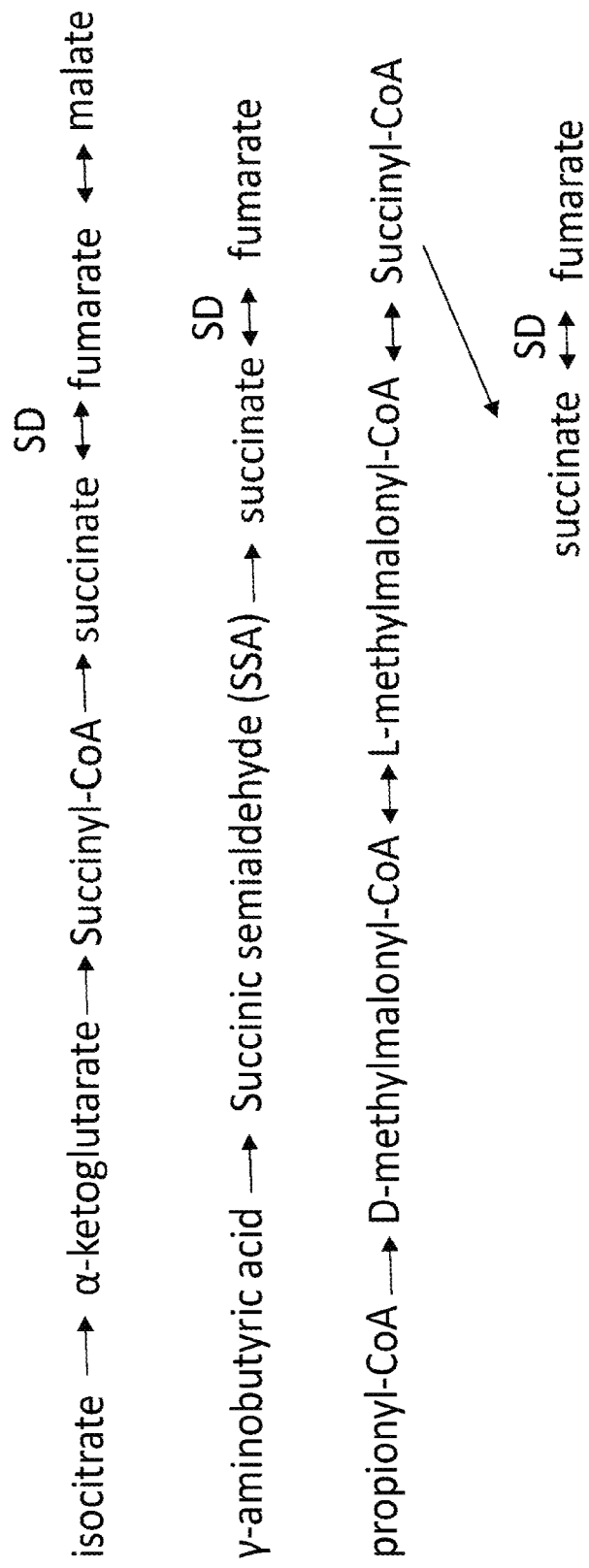
FIG. 1: Examples of biochemical pathways comprising succinate hydrogenase.

The present disclosure is based on the concept that damage to neural tissue initiates an immune response that attacks and kills neurons, resulting in progressive worsening of neurological symptoms. This concept led to the proposal that inhibition of, or a reduction in, the neuroimmune response may reduce further damage to neuronal tissue. The inventors have discovered that, surprisingly, regulation of succinate levels, and/or the activity of succinate dehydrogenase, may play a role in regulating the activation of microglia, a key component of the immune response in neural tissue. Moreover, the inventors have discovered that inhibition of the succinate dehydrogenase (SDH) pathway, following physical damage to nerve axons, improved the survival rate of the nerve cell bodies. Without being bound by theory, the inventors believe that such improvement in the survival rate is a result of a succinate-mediated decrease in a neural tissue-related immune response, for example decreased microglial cell activation. Accordingly, a method of this disclosure can generally be practiced by administering to a subject in need of such treatment, at least one compound that reduces the level of succinate, and/or that reduces the level or activity of succinate dehydrogenase, in the individual. Such treatment may reduce or inhibit an immune response in neural tissue, thereby ameliorating immune-mediated disease, such as an immune-mediated neurological disorder. Useful compounds may modulate biochemical pathways involved in the synthesis, or catabolism, of succinate, or biochemical pathways that comprise succinate dehydrogenase. This disclosure also discloses novel compounds that inhibit, or reduce, the activity of a biochemical pathway comprising succinate and/or succinate dehydrogenase. The disclosure also includes the use of such compounds for treating neurological disorders.

This invention is not limited to the particular embodiments described herein, as such may vary. The terminology used herein is for the purpose of describing particular embodiments only, and is not intended to be limiting, because the scope of the invention will be limited only by the claims.

As used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly, the terms "comprising," "including," and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The terms "individual", "subject", and "patient" are well-recognized in the art and are used interchangeably herein to refer to any animal susceptible to developing a neurological disorder. Examples of individuals, subjects, patients, and the like, suitable for treating using methods and compositions of this disclosure include, but are not limited to, humans and other primates, including non-human primates such as chimpanzees and other apes and monkey species; farm animals such as cattle, sheep, pigs, seals, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms individual, subject, patient, and the like, by themselves, do not denote a particular age, sex, or race. Thus, individuals of any age, whether male or female, are intended to be covered by the present disclosure and include, but are not limited to the elderly, adults, children, babies, infants, and toddlers. Likewise, the methods of this disclosure can be applied to any race, including, for example, Caucasian (white), African-American (black), Native American, Native Hawaiian, Hispanic, Latino, Asian, and European.

As used herein, "compound" means a chemical or biological molecule such as a simple or complex organic molecule, a peptide, a protein, an oligonucleotide, a prodrug, or pharmaceutically-acceptable salt thereof. Examples of such compounds include, but are not limited to, dimethyl malonate (DMM), oxaloacetic acid, octyl itaconate, and active metabolites and derivatives thereof.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

As used herein, the phrase "pharmaceutically-acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically-acceptable salts include the conventional non-toxic salts or the quaternary ammonium salts of the parent compound formed, for example, from non-toxic inorganic or organic acids. Such conventional nontoxic salts include those derived from inorganic acids, such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds suitable for use in contact with the tissues of human beings and animals without excessive toxicity, irritation, allergic response, or other problem or complication, commensurate with a reasonable benefit/risk ratio.

Pharmaceutically-acceptable salt forms of compounds provided herein are synthesized from the compounds disclosed herein, or derivatives thereof, that contain a basic or acidic moiety by conventional chemical methods. Generally, such salts are prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are known to those skilled in the art and are also found in at page 1418 of Remington's Pharmaceutical Sciences, 17th ed., Mack Publishing Company, Easton, Pa., 1985.

The term "prodrug" is intended to include any covalently bonded carriers that release an active parent drug of this disclosure in vivo when such prodrug is administered to a mammalian subject. Because prodrugs are known to enhance numerous desirable qualities of pharmaceuticals (i.e., solubility, bioavailability, half-life, manufacturing, etc.) the compounds of this disclosure may be delivered in prodrug form. Thus, this disclosure encompasses prodrugs of compounds of the invention, methods of delivering the same, and compositions containing the same. Prodrugs useful for practicing the disclosed methods of this disclosure may be prepared by modifying functional groups present in the compound in such a way that the modifications are cleaved, either in routine manipulation or in vivo, to an active compound of this disclosure. Prodrugs may include compounds of this disclosure wherein an acyl, hydroxy, amino, or sulfhydryl group is bonded to any group that, when the prodrug of this disclosure is administered to a mammalian subject, is cleaved to form a free acetyl, hydroxyl, free amino, or free sulfhydryl group, respectively. Examples of prodrugs include, but are not limited to, acetate, formate, and benzoate derivatives of alcohol and amine functional groups in the compounds of the present invention.

It will be appreciated by those skilled in the art that compounds of the invention having a chiral center may exist in, and may be isolated in, optically active and racemic forms. It is to be understood that the compounds of this disclosure encompass any racemic, optically-active, regioisomeric or stereoisomeric form, or mixtures thereof, which possess the therapeutically useful properties described herein. It is well known in the art how to prepare optically active forms (for example, by resolution of the racemic form by recrystallization techniques, by synthesis from optically-active starting materials, by chiral synthesis, or by chromatographic separation using a chiral stationary phase). It is also to be understood that the scope of this invention encompasses not only the various isomers, which may exist but also the various mixtures of isomers, which may be formed. For example, if the compound of this disclosure contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium Optical Resolution Procedures for Chemical Compounds: Optical Resolution Information Center, Manhattan College, Riverdale, N.Y., and in Enantiomers, Racemates and Resolutions, Jean Jacques, Andre Collet and Samuel H. Wilen; John Wiley & Sons, Inc., New York, 1981, which is incorporated in its entirety by this reference. Basically, the resolution of the compounds is based on the differences in the physical properties of diastereomers by attachment, either chemically or enzymatically, of an enantiomerically-pure moiety resulting in forms that are separable by fractional crystallization, distillation, or chromatography.

Compounds used in making the pharmaceutical compositions of this disclosure may be purchased commercially. The compounds of the present invention, including the salts and prodrugs of these compounds, may also be prepared in ways well known to those skilled in the art of organic synthesis. The compounds of the invention may be prepared using the reactions performed in solvents appropriate to the reagents and materials employed and suitable for the transformation being affected. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used.

Compounds used to practice the invention may be administered by various parenteral means. Pharmaceutical compositions suitable for parenteral administration include various aqueous media such as aqueous dextrose and saline solutions; glycol solutions are also useful carriers, and preferably contain a water-soluble salt of the active ingredient, suitable stabilizing agents, and if necessary, buffering agents. Antioxidizing agents, such as sodium bisulfate, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compounds useful for practicing the invention can be administered orally in solid dosage forms, such as capsules, tablets, and powders; or in liquid forms such as elixirs, syrups, and/or suspensions. Gelatin capsules can be used to contain the active ingredient and a suitable carrier such as, but not limited to, lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste or used to protect the active ingredients from the atmosphere, or to allow selective disintegration of the tablet in the gastrointestinal tract.

As used herein, a "biochemical pathway" is a series of enzyme-mediated reactions, and the related substrates and reaction products, where the product of one enzymatic reaction is used as the substrate in the next enzymatic reaction. The glycolytic pathway, which converts glucose into pyruvate and lactate, is one example of a well-known biochemical pathway. It will be understood by those skilled in the art that biochemical pathways often intersect with other biochemical pathways, and that enzymes, substrates, and enzymatic products can be associated with more than one biochemical pathway. Accordingly, for ease of discussion, biochemical pathways are often defined using end points, such as a starting substrate and an end product or action. For example, the glycolytic pathway is often defined as the series of enzymatic reactions that convert glucose into pyruvate.

Compounds useful for practicing methods of this disclosure are compounds that modulate biochemical pathways comprising succinate and/or succinate dehydrogenase. Succinate dehydrogenase (SDH), also referred to as succinate-coenzyme Q reductase (SQR), or respiratory Complex II, catalyzes the conversion of succinate into fumarate. Examples of subunits of human succinate dehydrogenase include, but are not limited to, UniProtKB database entries P31040 (SDHA_Human), P21912 (SDHB_Human), Q99643 (SDHC_Human), and O14521 (DHSD_Human). As used herein, a biochemical pathway comprising succinate means any series of enzyme-mediated reactions, and related substrates and reaction products, in which at least one of the substrates or reaction products is succinate. As used herein, a biochemical pathway comprising succinate dehydrogenase means any series of enzyme-mediated reactions, and the related substrates and reaction products, in which at least one of the enzymes is succinate dehydrogenase. In various aspects of the disclosure, a biochemical pathway comprising succinate dehydrogenase may refer to a series of enzymes, and related substrates or reaction products, that includes up to three enzymes upstream and/or downstream in the pathway from succinate dehydrogenase. Examples of pathways comprising succinate and succinate dehydrogenase are known to those skilled in the art. Specific examples of several such pathways are illustrated in FIG. 1.

Biochemical pathways comprising succinate can be involved in the synthesis of succinate, and/or the breakdown (i.e., catabolism) of succinate. Biochemical pathways comprising succinate dehydrogenase can be those that produce or regulate products/molecules involved in activation of microglia and/or astrocytes, or release of cytokines or other immunoregulatory molecules therefrom. Generally, activation refers to an enhanced ability of a microglial cell or astrocyte to perform a function beyond that present in their basal state. For microglia and astrocytes, activation is multi-dimensional, i.e., they proliferate, phagocytose, and release proinflammatory cytokines or growth factors. Upon activation of microglia, their cellular morphology changes from small cell body with fine processes to large cell body with amoeboid processes (hypertrophy and overexpression of intermediate filaments, known as "stellate morphology"). They also undergo rapid proliferation to substantially increase in cell number, and release cytokines such as IL-1, IL-18, and prostaglandin $D_2$. Activated astrocytes release neurotrophic factors such as transforming growth factor beta (TGF-β) and nerve growth factor (NGF), and show substantially elevated intracellular calcium ($Ca^{2+}$). In certain aspects, compounds useful for practicing the invention are those that reduce the level of succinate, or reduce the activity of succinate dehydrogenase, and that decrease or inhibit any of such microglial activities.

As used herein, a compound that "modulates" a biochemical pathway means the compound increases or decreases the activity of one or more enzymes in the biochemical pathway, and/or the compound increases or decreases the level of one or more substrates or products in the biochemical pathway. Preferred compounds to use in the methods disclosed herein are those that modulate: i) a biochemical pathway involved in the synthesis or catabolism of succinate; or, ii) a biochemical pathway comprising succinate dehydrogenase, such that the enzymatic activity of succinate dehydrogenase is reduced or inhibited.

Compounds that modulate succinate-related biochemical pathways may act by reducing the level (e.g., amount, concentration, etc.) or activity of enzymes necessary for the synthesis of succinate. Alternatively, such compounds may act by increasing the level (e.g., amount, concentration) or activity of enzymes that convert succinate into another molecule (e.g., fumarate), or enzymes involved in the catabolism of succinate.

As used herein, a reduction in SDH enzymatic activity refers to a level of SDH enzymatic activity at least 10% lower than the level observed in the subject when the compound is not administered to the subject (i.e., basal level). In preferred aspects of the invention, a compound used to practice the invention reduces the level of SDH enzymatic activity by at least 15%, at least 20%, at least 25%, at least 30%, at least 40%, at least 50%, at least 60%, at least 70%, at least 80%, or at least 90%, relative to the level observed in the subject when the compound is not present. As used herein, inhibition of SDH enzymatic activity refers to an undetectable level of SDH enzymatic activity, or any product produced using SDH, using assays known to those skilled in the art. Such assays can include, but are not limited to, in vitro assays (e.g., laboratory or bench assays) using, for example, synthetic substrates to measure enzymatic activity, as well as assays that measure the in vivo level of SDH substrate and/or product (e.g., succinate, fumarate, etc.).

Compounds that modulate biochemical pathways comprising succinate dehydrogenase may cause such modulation by acting on any component (e.g., enzyme, protein, molecule, etc.) in the biochemical pathway. In these methods, these compounds may act directly on succinate dehydrogenase to decrease or inhibit the enzymatic activity. Such direct interaction can include binding of the compound to succinate dehydrogenase and/or modification of succinate dehydrogenase. In these methods, these compounds may act on a component of the biochemical pathway, upstream or downstream of succinate dehydrogenase in the pathway. The terms "upstream" and "downstream" are commonly used in the art to refer to the relative position of molecules in a biochemical pathway. Substrates that are converted into products are generally considered to be upstream of the product. Products are generally considered to be downstream of substrates. For example, in the isocitrate biochemical pathway illustrated in FIG. 1, succinyl-CoA is considered to be downstream of isocitrate and α-ketoglutarate, but upstream of succinate and fumarate. It will be appreciated that some enzymes are bi-functional, meaning they can convert a substrate into a product, and the product back into the substrate. For such enzymes, the molecule being converted by an enzyme into a product is considered upstream in the reaction.

One aspect of the invention is a method of treating an immune-mediated disorder, in a subject by administering to a subject a therapeutically-effective amount of at least one compound that: i) reduces the level of succinate in the subject; and/or, ii) reduces the level or activity of succinate dehydrogenase in the subject. In one aspect, the immune-related disorder is a neurological disorder.

As used herein, the term "immune-mediated disorder" is a disorder resulting from an individuals' immune system attacking the individual's own tissue, such as tissue of the central or peripheral nervous system. As used herein, the phrase "neurological disorder" refers to any condition resulting from dysfunction in the brain or nervous system (e.g., spinal cord, cranial nerves, peripheral nerves, nerve roots, autonomic nervous system, neuromuscular junction, and muscles), that causes physical and/or psychological symptoms. Such symptoms may include, but are not limited to, physical symptoms (e.g., partial or complete paralysis, muscle weakness, seizures, pain), cognitive symptoms (e.g., confusion, loss of short-term or long-term memory, impaired judgement), emotional and behavioral symptoms (e.g., mood swings, depression, delusions, outbursts), and combinations and clusters thereof. In certain aspects, neurological disorders may result from an individual's immune system attacking neurological tissue.

Neurological disorders treatable using the methods disclosed herein can be congenital disorders (i.e., present at birth) or they can be acquired disorders (i.e., developed after birth). Moreover, neurological disorders treatable using methods of the invention can result from a variety of causes, including, but not limited to, genetic abnormalities, including chromosomal abnormalities, metabolic disorders, congenital malformations, toxins, nutritional deficiencies, infections, immune disorders, traumatic injuries, and neoplasms. Exemplary neurological disorders that are treated using the methods disclosed herein include, but are not limited to, neurological disorders comprising an immune response (i.e., a neurological disorder in which an immune response is involved as either the initial causative agent or is involved in response to an initial event such as a trauma, infection or disease), such as an immune response including microglial cells and/or astrocytes. Specific examples of neurological disorders that can be treated using methods of this disclosure include, but are not limited to, Alzheimer disease and other dementias, migraine and other headache disorders, multiple sclerosis, Parkinson's disease, neuroinfections, brain tumors, traumatic disorders of the nervous system (including head trauma and spinal cord injuries), and neurological disorders resulting from malnutrition.

As used herein, a "therapeutically-effective amount" of a compound means an amount of a compound that when administered to a subject, is sufficient to treat the subject for a neurological disorder, including treatment of related signs and symptoms, such as damage of neural tissue, neurodegeneration, physical symptoms, emotional symptoms, and or cognitive symptoms, in a subject, including one or more of the following:

1. preventing the development of, or reducing the risk of developing, a neurological disease or disorder. As used herein, the phrases "preventing the development of," and "reducing the risk of developing," mean preventing the clinical symptoms of a neurological disorder from developing in a subject. Prior to treatment, the subject may, but need not, exhibit one or more risk factors for developing a neurological disorder, such as damage of neural tissue, neurodegeneration, and the like.
2. inhibiting a neurological disorder. As used herein, the terms "inhibiting," "arresting," and the like, mean stopping the further development, or slowing the progression, of clinical symptoms of a neurological disorder; and,
3. reducing a neurological disorder. As used herein, the terms "reducing," "reversing," "alleviating," and the like, mean a decrease in, or a cessation of, the number, frequency, duration, or severity, of clinical symptoms of a neurological disorder.

A "therapeutically effective amount" of a compound disclosed herein, or a derivative or salt thereof, may vary for a particular subject, depending on such factors as the overall health and physical conditions of the subject, the extent of the neurological disorder, and the age of the subject. The "therapeutically effective amount" may fall within a broad range, based on factors such as those disclosed above, that can be determined through clinical trials, methods for which are known to those skilled in the art.

As has been previously discussed, administration of a compound of the disclosure may treat immune-related disease, such as neurological diseases, by reducing or inhibiting an immune response. Administration of at least one compound of this disclosure may reduce or inhibit an immune response in a subject by 1) reducing the amount (e.g., level or concentration) of SDH-related reactive oxygen species (ROS); 2) reducing the levels of, or inhibiting the production of, components of the immune system, such as cytokines; or, 3) reducing the levels of, or inhibiting, activation of immune cells such as microglial cells or astrocytes. Without being bound by theory, the inventors believe that these three areas are involved in regulation of immune responses in neural tissue. For example, conversion of succinate to fumarate by SDH is known to result in the production of ROS, which, perhaps through other intermediates such as hypoxia-inducible factor-1 alpha (HIF-1α), causes an increase in the level of IL-1. IL-1 is known to stimulate activation of microglial cells. Thus, in methods of the disclosure, administration of at least one compound to the subject reduces the level of ROS. In these methods, administration of at least one compound to the subject may reduce or inhibit the production or release of immunoregulatory molecules, such as cytokines, from microglial cells. In these methods, administration of at least one compound to the subject may inhibit activation of microglial cells. In these methods, administration of the at least one compound may reduce or inhibit the activation of astrocytes. Without intending to be bound by theory, reducing activation of microglial cells or astrocytes, may result from cells in these cellular populations having a higher threshold for responding to activating stimuli. Alternatively, reducing activation of microglial cells or astrocytes, may result from a smaller number of microglial cells or astrocytes to respond to an activating stimulus.

A related aspect of this disclosure is a method of reducing or preventing neuronal damage in a subject in need of such treatment by administering to the subject at least one compound that: i) reduces the level of succinate in the subject; and/or, ii) reduces the level or activity of succinate dehydrogenase in the subject.

In these methods, the neuronal damage may be the result of Alzheimer's disease or other dementias, multiple sclerosis, Parkinson's disease, neuroinfections, brain tumors, trauma (including head trauma and spinal cord injuries), or malnutrition.

Another related aspect of this disclosure is a method of inhibiting activation of a microglial cell by contacting the microglial cell with at least one compound that: i) reduces the level of succinate in the cell; and/or ii) reduces the level or activity of succinate dehydrogenase in the cell. In these methods, contact of the microglial cell with the compound may inhibit the production of one or more immunoregulatory molecules by the microglial cell and/or inhibit the production of cytokines by the microglial cell. These methods may be conducted in vitro or in vivo.

A related aspect of this disclosure is a method of reducing or preventing the production or release of one or more immunoregulatory molecules from a microglial cell by contacting the microglial cell with at least one compound that: i) reduces the level of succinate in the cell; and/or ii) reduces the level or activity of succinate dehydrogenase in the cell. In these methods, the immunoregulatory molecule(s) may comprise cytokines. Similarly, these methods may be conducted in vitro or in vivo.

A related aspect of this disclosure is a method of preventing the activation of an astrocyte in a system comprising at least one microglial cell and at least one astrocyte, by introducing into the system at least one compound that: i) reduces the level of succinate in the microglial cell; and/or ii) reduces the level or activity of succinate dehydrogenase in the microglial cell. In these methods, the system may be an in vitro system, for example one or more tissue culture dishes incubating these cells. Alternatively, the system can be in vivo, in an organism.

In any of the methods of this disclosure, the compound that is administered to the subject, or contacted with the cell(s) in vitro, may modulate the activity of an enzyme upstream or downstream of succinate dehydrogenase in the biochemical pathway. The enzyme being modulated may be up to three enzymes away from succinate dehydrogenase in the biochemical pathway. The compound may modulate the level of a substrate or product, upstream or downstream of succinate dehydrogenase in the biochemical pathway. In these methods, the compound may reduce or inhibit the enzymatic activity of succinate dehydrogenase. In these methods, the compound may act directly on succinate dehydrogenase. In these methods, the compound may be a specific inhibitor of succinate dehydrogenase. In these methods, the compound may reduce the level or activity of enzymes involved in the synthesis of succinate. In these methods, the compound may increase the level or activity of enzymes involved in the catabolism of succinate. In these methods, the compound may modulate a biochemical pathway comprising succinate dehydrogenase (SDH), such that the level or activity of succinate dehydrogenase is reduced. In these methods, the compound may act directly on succinate dehydrogenase to reduce or inhibit its activity.

Inhibitors of succinate dehydrogenase that are useful in any of the methods of this disclosure are known in the art and include those disclosed in U.S. Patent Publication Nos. US2017/0135977; US2017/0107380; US2012/0258989, each of which are incorporated herein by reference. Exemplary compounds for use in the methods of this disclosure include dimethyl malonate (DMM), oxaloacetic acid, octyl itaconate, or active metabolites, analogs, or derivatives thereof, or combinations thereof.

It is known that in some biochemical pathways, products of enzymatic reactions can modulate (i.e., increase or decrease) the activity of enzymes in the biochemical pathway, providing a feedback mechanism that regulates the overall activity or throughput of the biochemical pathway. Thus, in any of the methods of this disclosure, the administered compound can comprise a molecule (e.g., an enzyme, a product, a substrate) from the biochemical pathway. In these methods, the compound may comprise a prodrug, or an active metabolite, analog, or derivative of a molecule from the biochemical pathway.

In any of these methods, the biochemical pathway being modulated may comprise, for example, one or more molecules selected from the group consisting of succinate, malate, fumarate, α-ketoglutarate, isocitrate, citrate, L-methylmalonyl-CoA (MM-CoA), succinyl-CoA, succinyl-CoA:3-ketoacid CoA, succinic semialdehyde (SSA), and γ-aminobutyric acid (GABA).

In any of these methods, the biochemical pathway being modulated may comprise, for example, one or more enzymes selected from the group consisting of malate dehydrogenase, fumarase, fumarate reductase, α-ketoglutarate dehydrogenase, isocitrate dehydrogenase, aconitase, L-methylmalonyl-CoA (MM-CoA) mutase, succinyl-CoA ligase, succinyl-CoA:3-ketoacid CoA transferase, succinic semialdehyde dehydrogenase (SSADH), and γ-aminobutyric acid (GABA) transaminase.

In any of these methods, the compound may reduce the level of, or inhibit, the enzymatic activity of, for example, one or more enzymes selected from the group consisting of malate dehydrogenase, fumarase, fumarate reductase, α-ketoglutarate dehydrogenase, isocitrate dehydrogenase, aconitase, L-methylmalonyl-CoA (MM-CoA) mutase, succinyl-CoA ligase, succinyl-CoA:3-ketoacid CoA transferase, succinic semialdehyde dehydrogenase (SSADH), an γ-aminobutyric acid (GABA) transaminase.

In one aspect, a compound useful for practicing methods of the disclosure may decrease the level of activity of SDH by decreasing the level of SHD protein. Such compounds may comprise molecules, such as nucleic acid molecules, that inhibit transcription from a gene encoding the SDH protein, or that prevents translation of mRNA encoding the SDH protein. Such therapeutic nucleic acid molecules are known to those skilled in the art, and comprise, for example, siRNA, miRNA, shRNA, ribozymes, and aptamers.

In any of the methods of treating a subject disclosed herein, administration of the compound may prevent the development of, or reduce the risk of developing, neuronal damage. This includes preventing the development of the clinical symptoms of neuronal damage in a subject. In any of these methods, administration of the compound may cause a decrease in, or a cessation of, the number, frequency, duration, or severity, of one or more clinical symptoms of neuronal damage.

In any of these methods of treating a subject, administration of the compound may reduce or inhibit an immune response. In these methods, administration of the compound may inhibit activation of one or more cells of the immune system such as microglial cells or astrocytes. In these methods, administration of the compound may inhibit the production or release of cytokines from a cell of the immune system such as a microglial cell or an astrocyte. In these methods, administration of the compound may reduce or inhibit the activation of microglial cells. In these methods, administration of the compound may reduce or inhibit the release of immunoregulatory molecules (e.g., cytokines) from microglial cells. In these methods, administration of the compound may reduce or inhibit the activation of astrocytes.

Compounds useful in the methods of this disclosure, can be incorporated into pharmaceutical compositions or formulations. Such pharmaceutical compositions/formulations are useful for administration to a subject, in vivo or ex vivo. Pharmaceutical compositions and formulations include carriers or excipients for administration to a subject. As used herein the terms "pharmaceutically acceptable" and "physiologically acceptable" mean a biologically compatible formulation, gaseous, liquid or solid, or mixture thereof, which is suitable for one or more routes of administration, in vivo delivery or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions. The formulations may, for convenience, be prepared or provided as a unit dosage form. In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient in a free-flowing form such as a powder or granules, optionally mixed with a binder, lubricant, inert diluent, preservative, surface-active or dispersing agent. Molded tablets may be produced by molding, in a suitable apparatus, a mixture of powdered compound moistened with an inert liquid diluent. The tablets may optionally be coated or scored and may be formulated to provide a slow or controlled release of the active ingredient therein.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone. Supplementary active compounds (e.g., preservatives, antioxidants, antimicrobial agents including biocides and biostats such as antibacterial, antiviral and antifungal agents) can also be incorporated into the compositions. Preservatives and other additives include, for example, antimicrobials, anti-oxidants, chelating agents and inert gases (e.g., nitrogen). Pharmaceutical compositions may therefore include preservatives, antimicrobial agents, anti-oxidants, chelating agents and inert gases.

Preservatives can be used to inhibit microbial growth or increase stability of the active ingredient thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

Pharmaceutical compositions can optionally be formulated to be compatible with a particular route of administration. Exemplary routes of administration include administration to a biological fluid, an immune cell (e.g., T or B cell) or tissue, mucosal cell or tissue (e.g., mouth, buccal cavity, labia, nasopharynx, esophagus, trachea, lung, stomach, small intestine, vagina, rectum, or colon), neural cell or tissue (e.g., ganglia, motor or sensory neurons) or epithelial cell or tissue (e.g., nose, fingers, ears, cornea, conjunctiva, skin or dermis). Thus, pharmaceutical compositions include carriers (excipients, diluents, vehicles or filling agents) suitable for administration to any cell, tissue or organ, in vivo, ex vivo (e.g., tissue or organ transplant) or in vitro, by various routes and delivery, locally, regionally or systemically.

Exemplary routes of administration for contact or in vivo delivery into which a succinate dehydrogenase modulating compound can optionally be formulated include inhalation, respiration, intubation, intrapulmonary instillation, oral (buccal, sublingual, mucosal), intrapulmonary, rectal, vaginal, intrauterine, intradermal, topical, dermal, parenteral (e.g., subcutaneous, intramuscular, intraperitoneal, intravenous, intradermal, intraocular, intratracheal and epidural), intranasal, intrathecal, intraarticular, intracavity, transdermal, iontophoretic, ophthalmic, optical (e.g., corneal), intraglandular, intraorgan, intralymphatic.

Formulations suitable for parenteral administration include aqueous and non-aqueous solutions, suspensions or emulsions of the compound, which may include suspending agents and thickening agents, which preparations are typically sterile and can be isotonic with the blood of the intended recipient. Non-limiting illustrative examples of aqueous carriers include water, saline (sodium chloride solution), dextrose (e.g., Ringer's dextrose), lactated Ringer's, fructose, ethanol, animal, vegetable or synthetic oils. Examples of non-aqueous solvents are propylene glycol, polyethylene glycol, vegetable oils such as olive oil, and injectable organic esters such as ethyl oleate. Intravenous vehicles include fluid and nutrient replenishers, electrolyte replenishers (such as those based on Ringer's dextrose). The formulations may be presented in unit-dose or multi-dose kits, for example, ampules and vials, and may be stored in a freeze-dried (lyophilized) condition requiring addition of a sterile liquid carrier, for example, water for injections, prior to use.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, pastes, lotions, oils or creams as generally known in the art.

For topical administration, for example, to skin, pharmaceutical compositions typically include ointments, creams, lotions, pastes, gels, sprays, aerosols or oils. Carriers which may be used include Vaseline, lanolin, polyethylene glycols, alcohols, transdermal enhancers, and combinations thereof. An exemplary topical delivery system is a transdermal patch containing an active ingredient.

For oral administration, pharmaceutical compositions include capsules, cachets, lozenges, tablets or troches, as powder or granules. Oral administration formulations also include a solution or a suspension (e.g., aqueous liquid or a non-aqueous liquid; or as an oil-in-water liquid emulsion or a water-in-oil emulsion).

For airway or nasal administration, pharmaceutical compositions can be formulated in a dry powder for delivery, such as a fine or a coarse powder having a particle size, for example, in the range of 20 to 500 microns which is administered in the manner by inhalation through the airways or nasal passage. Depending on delivery device efficiency, effective dry powder dosage levels typically fall in the range of about 10 to about 100 mg. Appropriate formulations, wherein the carrier is a liquid, for administration, as for example, a nasal spray or as nasal drops, include aqueous or oily solutions of the active ingredient.

For airway or nasal administration, aerosol and spray delivery systems and devices, also referred to as "aerosol generators" and "spray generators," such as metered dose inhalers (MDI), nebulizers (ultrasonic, electronic and other nebulizers), nasal sprayers and dry powder inhalers can be used. MDIs typically include an actuator, a metering valve, and a container that holds a suspension or solution, propellant, and surfactant (e.g., oleic acid, sorbitan trioleate, lecithin). Activation of the actuator causes a predetermined amount to be dispensed from the container in the form of an aerosol, which is inhaled by the subject. MDIs typically use liquid propellant and typically, MDIs create droplets that are 15 to 30 microns in diameter, optimized to deliver doses of 1 microgram to 10 mg of a therapeutic. Nebulizers are devices that turn medication into a fine mist inhalable by a subject through a face mask that covers the mouth and nose. Nebulizers provide small droplets and high mass output for delivery to upper and lower respiratory airways. Typically, nebulizers create droplets down to about 1 micron in diameter.

Dry-powder inhalers (DPI) can be used to deliver the compounds of the invention, either alone or in combination with a pharmaceutically acceptable carrier. DPIs deliver active ingredient to airways and lungs while the subject inhales through the device. DPIs typically do not contain propellants or other ingredients, only medication, but may optionally include other components. DPIs are typically breath-activated, but may involve air or gas pressure to assist delivery.

For rectal administration, pharmaceutical compositions can be included as a suppository with a suitable base comprising, for example, cocoa butter or a salicylate. For vaginal administration, pharmaceutical compositions can be included as pessaries, tampons, creams, gels, pastes, foams or spray formulations containing in addition to the active ingredient a carrier, examples of appropriate carriers which are known in the art.

Pharmaceutical formulations and delivery systems appropriate for the compositions and methods of the invention are known in the art (see, e.g., Remington: The Science and Practice of Pharmacy (2003) 20.sup.th ed., Mack Publishing Co., Easton, Pa.; Remington's Pharmaceutical Sciences (1990) 18.sup.th ed., Mack Publishing Co., Easton, Pa.; The Merck Index (1996) 12.sup.th ed., Merck Publishing Group, Whitehouse, N.J.; Pharmaceutical Principles of Solid Dosage Forms (1993), Technonic Publishing Co., Inc., Lancaster, Pa.; Ansel and Stoklosa, Pharmaceutical Calculations (2001) 11.sup.th ed., Lippincott Williams & Wilkins, Baltimore, Md.; and Poznansky et al., Drug Delivery Systems (1980), R. L. Juliano, ed., Oxford, N.Y., pp. 253-315).

Compounds useful for practicing the methods of this disclosure may be packaged in unit dosage forms for ease of administration and uniformity of dosage. A "unit dosage form" as used herein refers to a physically discrete unit suited as unitary dosages for the subject to be treated; each unit containing a predetermined quantity of compound optionally in association with a pharmaceutical carrier (excipient, diluent, vehicle or filling agent) which, when administered in one or more doses, is calculated to produce a desired effect (e.g., prophylactic or therapeutic effect or benefit). Unit dosage forms can contain a daily dose or unit, daily sub-dose, or an appropriate fraction thereof, of an administered compound. Unit dosage forms also include, for example, capsules, troches, cachets, lozenges, tablets, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Unit dosage forms further include compounds for transdermal administration, such as "patches" that contact with the epidermis of the subject for an extended or brief period of time. The individual unit dosage forms can be included in multi-dose kits or containers. Pharmaceutical formulations can be packaged in single or multiple unit dosage forms for ease of administration and uniformity of dosage.

In the methods of the invention, compounds that reduce the level of succinate, and/or reduce the level or activity of succinate dehydrogenase may be administered in accordance with the methods at any frequency as a single bolus or multiple dose e.g., one, two, three, four, five, or more times hourly, daily, weekly, monthly or annually or between about 1 to 10 days, weeks, months, or for as long as appropriate. Exemplary frequencies are typically from 1-7 times, 1-5 times, 1-3 times, 2-times or once, daily, weekly or monthly. Timing of contact, administration ex vivo or in vivo delivery can be dictated by the infection, reactivation, pathogenesis, symptom, pathology or adverse side effect to be treated. For example, an amount can be administered to the subject substantially contemporaneously with, or within about 1-60 minutes or hours of the onset of a symptom of neurological disease or disorder.

Doses may vary depending upon whether the treatment is therapeutic or prophylactic, the onset, progression, severity, frequency, duration, probability of or susceptibility of the symptom, the type of virus infection, reactivation or pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history). Dose amount, frequency or duration may be increased or reduced, as indicated by the clinical outcome desired, status of the infection, reactivation, pathology or symptom, or any adverse side effects of the treatment or therapy. The skilled artisan will appreciate the factors that may influence the dosage, frequency and timing required to provide an amount sufficient or effective for providing a prophylactic or therapeutic effect or benefit.

Certain features of this disclosure, which are, for clarity, described in the context of separate aspect of this disclosure, may also be provided in combination in a single aspect or embodiment. Conversely, various features of this disclosure, which are, for brevity, described in the context of a single aspect, may also be provided separately or in any suitable sub-combination. All combinations of the aspect and embodiments of this disclosure are specifically embraced by this disclosure and are disclosed herein just as if each and every combination was individually and explicitly disclosed. In addition, all sub-combinations are also specifically embraced by this disclosure and are disclosed herein just as if each and every such sub-combination was individually and explicitly disclosed herein.

The publications discussed herein are provided solely for their disclosure prior to the filing date of the present application. Nothing herein is to be construed as an admission that this disclosure is not entitled to antedate such publication by virtue of prior invention. Further, the dates of publication provided may be different from the actual publication dates, which may need to be independently confirmed. All publications mentioned herein are incorporated herein by reference to disclose and describe the methods and/or materials in connection with which the publications are cited.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

EXAMPLES

Example 1

Metabolic Profiling During Hibernation

Figures 2A, 2B:
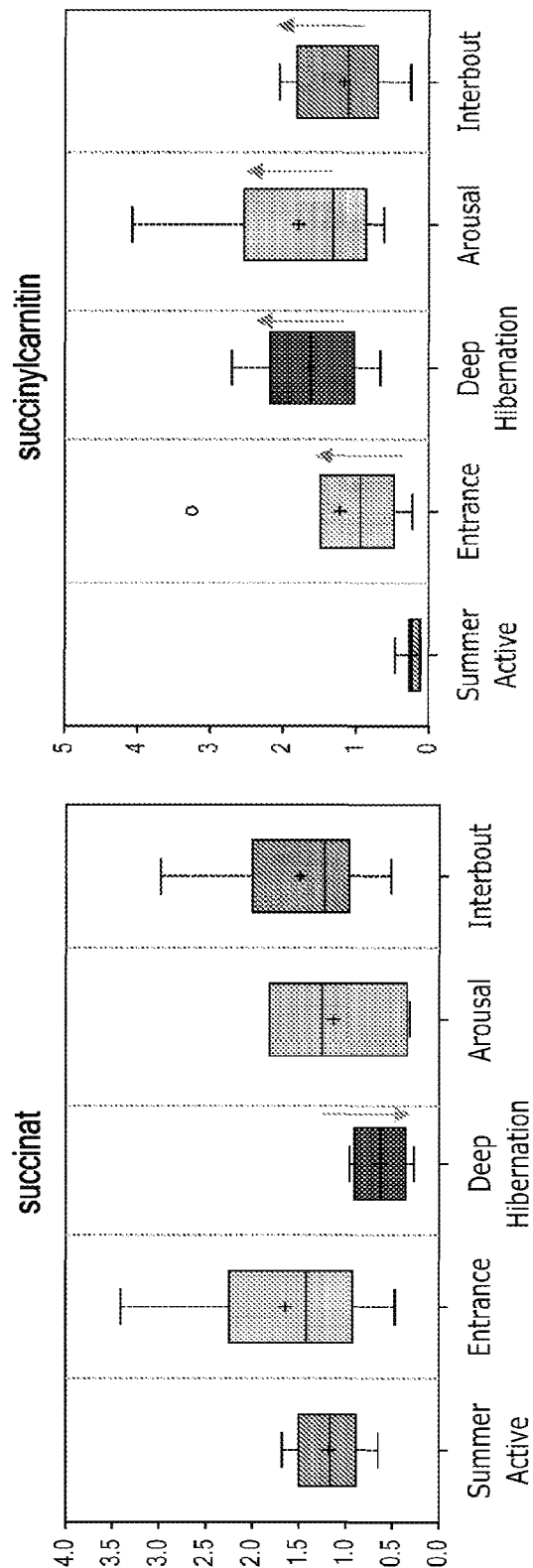
FIGS. 2A and 2B show the results of characterization of metabolomic profiling of ground squirrel (GS) retinas.
Figure 3:
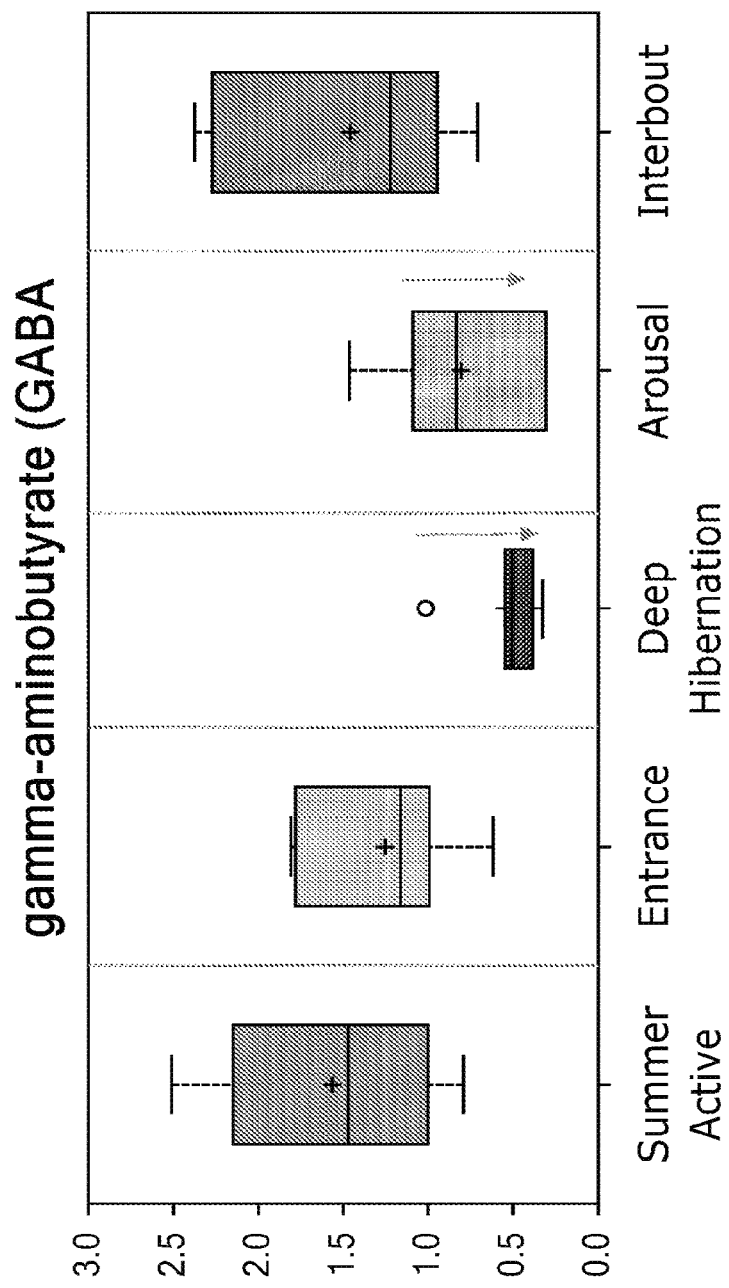
FIG. 3 shows a drastic decrease in the levels of gamma-aminobutyric acid (GABA) in hibernating retinal tissues.

Metabolomic profiling of ground squirrel (GS) retinas was performed during 5 different stages during the season: summer active, entrance of hibernation, deep hibernation, arousing from hibernation, and interbout arousal. The data obtained from this profiling showed significantly decreased level of succinate in the retinal tissues during deep hibernation (FIG. 2A), along with increased levels of succinyl-carnitin (FIG. 2B). These results suggested that the activity of succinate dehydrogenase (SDH), which converts succinate to fumarate, was reduced. Such regulation has also been observed in the liver and muscle of hibernating (Jason, et al., 2013. *Regulation of succinate-fueled mitochondrial respiration in liver and skeletal muscle of hibernating thirteen-lined ground squirrels.* Journal of Experimental Biology, 10.1242/jeb.078519). Further, when the SDH activity from the retinas of awake vs hibernating GS was measured, it was found that SDH activity in hibernating retinal tissues was reduced. Additionally, a drastic decrease in the levels of gamma-aminobutyric acid (GABA), a known source of succinate, was also observed (FIG. 3).

Example 2

Figure 4:
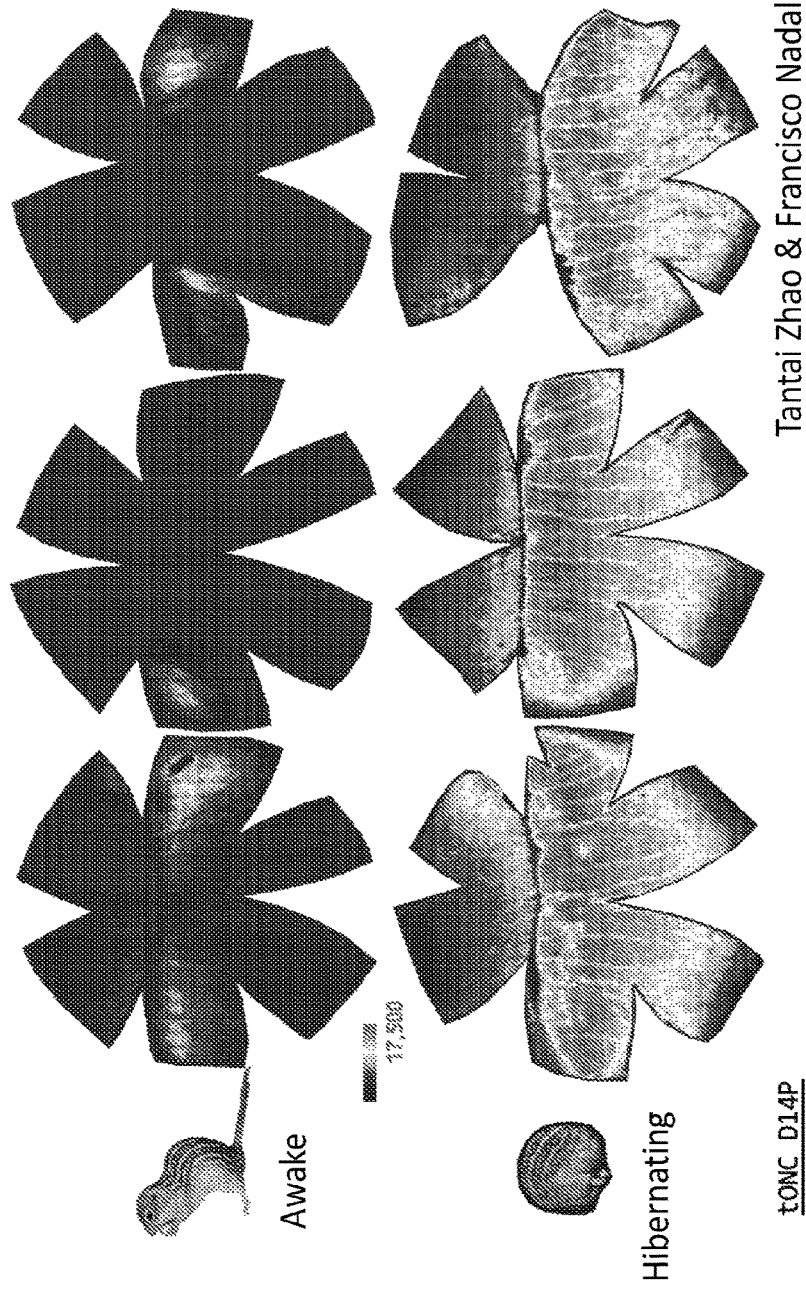
FIG. 4 shows retina ganglion cells (RGCs) survive optic nerve crush (ONC) during hibernation.

Lower Succinate During Hibernation Leads to Immune Suppression and Neuroprotection Previous work has shown that succinate regulates macrophages, causing them to switch between pro-inflammatory and anti-inflammatory states (Mills, et al., (2016) *Succinate Dehydrogenase Supports Metabolic Repurposing of Mitochondria to Drive Inflammatory Macrophages.* Cell, 67(2); 457-470.e13). Thus, the inventors hypothesized that immune regulation due to reduced succinate levels may occur in the retina during hibernation, and that this may subsequently affect cellular response to neural injury. To test this hypothesis, optic nerve crush (ONC), a classic axonal injury experiment, was performed in awake and in hibernating ground squirrels. Retina ganglion cells (RGCs) appeared to survive ONC during hibernation (FIG. 4).

Figure 5A:
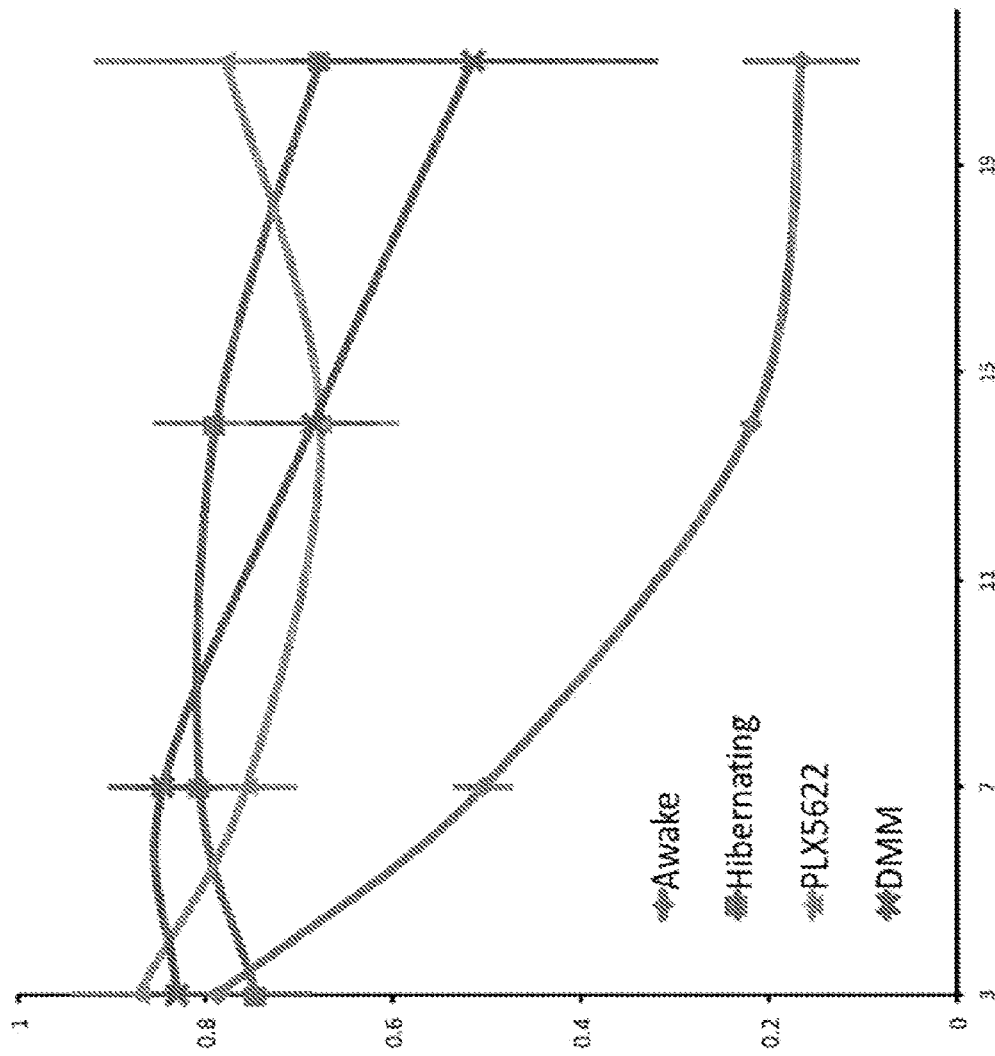
FIGS. 5A and 5B show the results of testing RGC survival and response following optic nerve injury.

Intriguingly, a key cellular response difference between awake and hibernating animals to ONC is microglial aggregation and activation, in line with the hypothesis that low succinate level during hibernation may prevent microglia from activation in response to injury. To further test this hypothesis, a second experiment was done in which dimethyl malonate (DMM), an inhibitor of SDH, was injected into the eye before and after the ONC surgery in awake animals to create a lower succinate condition, thereby mimicking hibernation. This treatment significantly improved RGC survival after ONC in awake animals (FIG. 5A).

To further examine the role of microglia, microglia were pharmacologically eliminated before ONC surgery in awake animals. Such treatment achieved similar protection of RGCs after ONC (FIG. 5A).

Figure 5B:
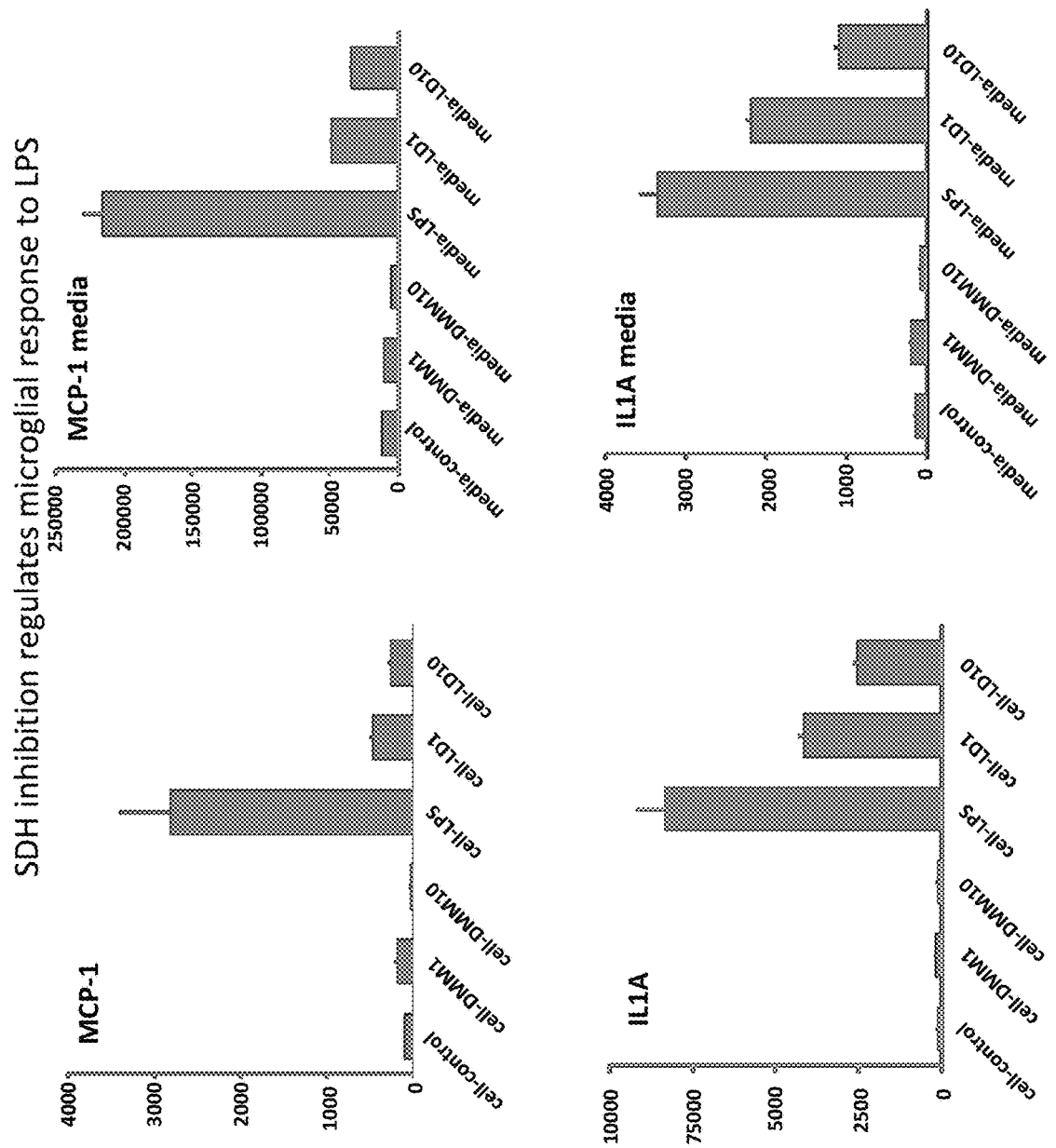

The direct effect of DMM on microglia was examined by conducting an in vitro experiment using a microglia cell line (BV2). It was found that DMM at the concentration of 1 or 10 mM significantly attenuated the response of microglia to LPS (a bacterial toxin that triggers an inflammatory response from microglia, releasing many inflammatory cytokines) (FIG. 5B). Thus, the results suggest that metabolic adaptation during hibernation (lower succinate) leads to local immune suppression (lower microglia activity), which in turn protects neurons from death after axonal injury. The results further suggest that mimicking hibernation through pharmacological means is a useful method of neural protection.

Example 3

Reduction of Succinate Dehydrogenase Activity Reduces Reactive Oxygen Species (ROS) and Cytokine Production It is known in the art that a key event in the LPS-induced macrophage activation is the over-production of mitochondrial ROS driven by the hyperpolarization of mitochondrial membrane potential and SDH-accelerated succinate oxidation (Mills et al., 2016). However, for the retina, it is challenging to perform live ROS measurement, because enucleation causes an acute ROS surge due to severing of the optic nerve. Thus, a method was developed to visualize in situ mitochondrial ROS production in thirteen lined ground squirrel (TLGS) retina with optic nerve crush (ONC), that used a mitochondrial ROS dye—MitoNeoD (Shchepinova et al., 2017). This method successfully revealed that following partial ONC in active TLGSs, a high level of mitochondrial ROS was produced in the injured side of the retina (FIG. 6A); in contrast, retina from torpid TLGSs did not show elevated mitochondrial ROS production with the same ONC injury FIG. 6(B). Surprisingly, in active TLGSs with ONC, intraocular injection of an SDH antagonist, DMM significantly alleviated ROS production (FIG. 6C). In active TLGS retina with partial ONC injuries, it was observed that above the optic nerve fiber/RGC layers there were cells decorated with bright MitoNeoOH (oxidized and fluorescent form of MitoNeoD) signals (arrows in FIG. 6D) overlapping with a mitochondrial protein marker (TOM20) (FIGS. 7A, 7B, and 7C). These cells were then confirmed to be mostly microglial cells (FIGS. 7D, 7E, and 7F). It was then confirmed that intraocular injection of DMM indeed lowered SDH activity in the retina of ONC-injured active TLGSs (FIG. 8B). Subsequently, using a microglial cell line (mouse BV-2), it was found that DMM effectively reduced LPS-induced production of pro-inflammatory cytokines, such as MCP-1, IL-1α, IL-6, but not TNFα from microglial cells. Taken together, these results suggest that SDH-driven mitochondrial ROS overproduction is a key mechanism modulating ONC-triggered microglial pro-inflammatory activation, while targeting this pathway by SDH antagonist DMM may emulate the protective effects of hibernation.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of the invention disclosed herein.

What is claimed:

1. A method of inhibiting activation of microglial cells, comprising contacting the microglial cells with a compound that decreases the level of succinate in the cells, or that reduces the activity of succinate dehydrogenase, wherein the compound comprises dimethyl malonate (DMM), oxaloacetic acid, or octyl itaconate.

2. The method of claim 1, wherein inhibition of activation comprises reducing or preventing the release of cytokines from the microglial cells.

3. A method of preventing the activation of an astrocyte in a system comprising microglial cells and astrocytes, comprising introducing into the system a compound that decreases the level of succinate in the cells, or that reduces the activity of succinate dehydrogenase, wherein the compound comprises dimethyl malonate (DMM), oxaloacetic acid, or octyl itaconate.

4. The method of claim 1, wherein the compound modulates a biochemical pathway comprising succinate.

5. The method of claim 1, wherein the compound modulates the activity of an enzyme upstream of succinate dehydrogenase in the biochemical pathway.

6. The method of claim 1, wherein the compound modulates the activity of an enzyme downstream of succinate dehydrogenase in the biochemical pathway.

7. The method of claim 1, wherein the biochemical pathway comprises at least one molecule selected from the group consisting of α-ketoglutarate, succinic semialdehyde, and methylmalonyl-CoA.

8. The method of claim 1, wherein the compound acts directly on succinate dehydrogenase.

9. The method of claim 1, wherein the compound inhibits the enzymatic activity of succinate dehydrogenase.

10. The method of claim 1, wherein the compound comprises a molecule from the biochemical pathway comprising succinate dehydrogenase, or a prodrug, or active metabolite, analog or derivative thereof.

11. The method of claim 1 or 3, wherein the compound comprises dimethyl malonate (DMM), or an active metabolite, analog, or derivative thereof.

12. The method of claim 1, wherein the compound comprises oxaloacetic acid, octyl itaconate, or an active metabolite, analog, or derivative thereof.

\* \* \* \* \*